US012616457B2

(12) United States Patent (10) Patent No.: US 12,616,457 B2

Papenfuss (45) Date of Patent: May 5, 2026

(54) CUTTING HEAD FOR TISSUE COLLECTION DEVICE

(71) Applicant: Medimetrix LLC, Naples, FL (US)

(72) Inventor: Erik Papenfuss, Naples, FL (US)

(73) Assignee: Medimetrix LLC, Naples, FL (US)

( * ) Notice: Subject to any disclaimer, the term of this patent is extended or adjusted under 35 U.S.C. 154(b) by 1092 days.

(21) Appl. No.: 17/625,241

(22) PCT Filed: Sep. 10, 2019

(86) PCT No.: PCT/US2019/050310

§ 371 (c)(1),
(2) Date: Jan. 6, 2022

(87) PCT Pub. No.: WO2021/050046

PCT Pub. Date: Mar. 18, 2021

(65) Prior Publication Data

US 2022/0287693 A1 Sep. 15, 2022

(51) Int. Cl.
A61B 10/02 (2006.01)
A61B 17/16 (2006.01)

(52) U.S. Cl.
CPC ........ A61B 10/025 (2013.01); A61B 17/1615 (2013.01); A61B 17/1631 (2013.01); (Continued)

(58) Field of Classification Search
None
See application file for complete search history.

(56) References Cited

U.S. PATENT DOCUMENTS

| 3,366,559 A | | 1/1968 | Hughes et al. |
| 5,190,548 A | * | 3/1993 | Davis .................... B23B 31/005 606/80 |

(Continued)

FOREIGN PATENT DOCUMENTS

| WO | 03101308 A1 | 12/2003 |
| WO | 2012047984 A1 | 4/2012 |
| WO | 2015109100 A1 | 7/2015 |

OTHER PUBLICATIONS

International Preliminary Report on Patentability and Written Opinion for International Application No. PCT/US2019/050310, issued Mar. 15, 2022, 7 pages.

(Continued)

*Primary Examiner* — Jacqueline Cheng
*Assistant Examiner* — Jairo H Portillo
(74) *Attorney, Agent, or Firm* — CM Law, LLP

(57) ABSTRACT

An instrument for collecting tissue from a body cavity includes a hollow tubular body. The tubular body has a tubular wall that extends between a proximal-most end and a distal-most end of the tubular body. The tubular wall surrounds a passage that extends to the distal end portion of the tubular body. The tubular body can be a non-bending shaft, or a shaft having an articulating section that allows a portion of the tubular body to articulate relative to the proximal end portion. The distal end portion includes a core drill with a cutting tip. The cutting tip defines a first aperture, a second aperture opposite the first aperture, and a web extending between the first aperture and the second aperture. The web tapers to a drill point at the distal-most end of the tubular body.

33 Claims, 6 Drawing Sheets

(52) U.S. Cl.
CPC ...... *A61B 17/1635* (2013.01); *A61B 17/1637*
(2013.01); *A61B 2010/0258* (2013.01)

(56) References Cited

U.S. PATENT DOCUMENTS

| | | | | |
|---|---|---|---|---|
| 5,269,785 | A | * | 12/1993 | Bonutti ................ A61B 10/025 |
| | | | | 606/167 |
| 5,366,468 | A | * | 11/1994 | Fucci ............... A61B 17/32002 |
| | | | | 606/180 |
| 5,556,399 | A | * | 9/1996 | Huebner .............. A61B 10/025 |
| | | | | 408/207 |
| 5,833,628 | A | * | 11/1998 | Yuan .................. A61B 17/1664 |
| | | | | 606/180 |
| 5,851,208 | A | * | 12/1998 | Trott ................ A61B 17/32002 |
| | | | | 606/80 |
| 5,954,671 | A | * | 9/1999 | O'Neill .............. A61B 17/1637 |
| | | | | 606/179 |
| 6,139,509 | A | * | 10/2000 | Yuan .................. A61B 17/1664 |
| | | | | 606/180 |
| 6,238,400 | B1 | | 5/2001 | Bays |
| 7,462,181 | B2 | | 12/2008 | Kraft et al. |
| 8,002,733 | B2 | | 8/2011 | Kraft et al. |
| 8,043,253 | B2 | | 10/2011 | Kraft et al. |
| 8,109,919 | B2 | | 2/2012 | Kraft et al. |
| 8,366,559 | B2 | | 2/2013 | Papenfuss et al. |
| 8,852,119 | B2 | | 10/2014 | Wawrzyniak et al. |
| 9,131,925 | B2 | | 9/2015 | Kraft et al. |
| 10,368,880 | B1 | * | 8/2019 | Alruhaimi .......... A61B 17/1637 |
| 2002/0038129 | A1 | | 3/2002 | Peters et al. |
| 2002/0172923 | A1 | * | 11/2002 | Strong ................ A61C 8/0089 |
| | | | | 433/165 |
| 2003/0199879 | A1 | | 10/2003 | Spranza |
| 2004/0191897 | A1 | * | 9/2004 | Muschler ......... A61B 17/32002 |
| | | | | 435/325 |
| 2004/0267154 | A1 | | 12/2004 | Sutton et al. |
| 2006/0111724 | A1 | * | 5/2006 | Yeung Wai Ping . A61C 8/0089 |
| | | | | 606/80 |
| 2006/0204021 | A1 | | 9/2006 | Okabayashi et al. |
| 2008/0177200 | A1 | | 7/2008 | Ikehara et al. |
| 2009/0105775 | A1 | | 4/2009 | Mitchell et al. |
| 2011/0184312 | A1 | | 7/2011 | Moran |
| 2011/0319896 | A1 | * | 12/2011 | Papenfuss .......... A61B 17/1631 |
| | | | | 606/79 |
| 2012/0116247 | A1 | * | 5/2012 | Wawrzyniak ........ A61B 10/025 |
| | | | | 600/567 |
| 2013/0317507 | A1 | * | 11/2013 | Khanna .............. A61B 17/1635 |
| | | | | 606/80 |
| 2015/0032139 | A1 | * | 1/2015 | Sjostrom ................ A61M 1/74 |
| | | | | 606/171 |
| 2015/0057664 | A1 | * | 2/2015 | Scianamblo ........... B23B 51/02 |
| | | | | 606/80 |
| 2015/0201915 | A1 | * | 7/2015 | Akerfeldt .......... A61B 10/0266 |
| | | | | 600/567 |
| 2015/0297243 | A1 | * | 10/2015 | Kulas .................... B23C 5/1009 |
| | | | | 606/80 |
| 2016/0000991 | A1 | | 1/2016 | Kraft et al. |
| 2016/0074021 | A1 | | 3/2016 | Dejima et al. |
| 2016/0296241 | A1 | | 10/2016 | Koljaka et al. |
| 2016/0325018 | A1 | | 11/2016 | Assell et al. |
| 2017/0311936 | A1 | | 11/2017 | Suzuki |
| 2018/0049727 | A1 | | 2/2018 | Papenfuss et al. |
| 2020/0113582 | A1 | | 4/2020 | Kulas et al. |

OTHER PUBLICATIONS

European Communication Pursuant to Article 94(3) for European Application No. 17 764 691.6, dated Aug. 3, 2020, 5 pages.
International Preliminary Report on Patentability and Written Opinion for International Application No. PCT/US2017/047265, issued Feb. 19, 2019, 10 pages.
International Search Report and Written Opinion for International Application No. PCT/US2017/047265, mailed Jan. 22, 2018, 17 pages.
Invitation to Pay Additional Fees and Partial International Search Report mailed Nov. 20, 2017, 12 pages.
Kraft et al., "Development of the "MarrowMiner": A novel, minimally invasive device for the harvest of bone marrow. From benchtop, to animal studies, through FDA approval and human evaluation", Feb. 2010, p. S167, vol. 16(2), Supplement 2, Biology of Blood and Marrow Transplantation, 2 pages.
Entire patent prosecution history of U.S. Appl. No. 15/240,080, filed Aug. 18, 2016, entitled, "Flexible Tissue Collection Device.".
International Search Report and Written Opinion for International Application No. PCT/US2019/050310, dated Nov. 19, 2019, 9 pages.
European Communication Pursuant to Article 94(3) for European Application No. 21 210 571.2, dated May 10, 2023, 7 pages.
Intent to Grant and Search Report issued in China Application No. 201980004835.5 (English version), dated Aug. 8, 2025 (9 pages).
Office Action issued in China Application No. 201980004835.5 (English version), dated Feb. 2, 2025 (12 pages).

* cited by examiner

ADVANCE COLLECTION INSTRUMENT TO BONE — 1000

ENTER BONE CAVITY — 2000

COLLECT BONE MARROW — 3000

WITHDRAW COLLECTION INSTRUMENT — 4000

REMOVE BONE MARROW FROM SHAFT — 5000

CUTTING HEAD FOR TISSUE COLLECTION DEVICE

This application is a U.S. National Phase application of PCT International Application No. PCT/US2019/050310, filed Sep. 10, 2019, which is incorporated by reference herein.

FIELD

The present disclosure relates generally to instrumentation for collecting tissue from a body cavity, and more particularly to a cutting head for collecting tissue in a preserved state from bone.

BACKGROUND

Bone marrow, which is produced and stored inside bone, can be harvested and used for different purposes, including the treatment of congenital defects and diseases, and reconstruction of bone. Bone marrow contains useful components, including hematopoietic stem cells and blood cells. Conventional methods for harvesting bone marrow have historically relied on the use of needles. A needle is advanced through the patient's skin and the wall of a bone until the needle tip enters into the bone cavity containing the marrow. Typically, the needle is advanced into the donor's pelvis, but the needle can also be inserted into other bones. Once the needle penetrates into the bone cavity, the needle advances in a linear path, and the marrow is harvested by aspiration.

Bone marrow harvesting by aspiration often yields a relatively small amount of stem cells because the concentration of stem cells at specific locations is low. To harvest a sufficient amount of marrow and stem cells, the physician must draw a significant volume of marrow which is greater than can be drawn from a single aspiration at one location. Therefore, to collect a sufficient volume of marrow and stem cells, the needle must be inserted into the bone at multiple locations within the bone cavity to draw bone marrow from different areas. This requires multiple punctures through the outer cortex and into the bone cavity to collect the required volume of marrow. Multiple punctures can be time consuming and labor intensive for physicians performing the harvesting. In addition, multiple punctures cause a great deal of pain to the donor and require a long recovery time after the patient is taken off of general anesthesia.

U.S. Pat. No. 7,462,181 to Daniel Kraft and James Hole (hereinafter, "the '181 Patent") describes an alternative device for aspirating bone marrow or tissue from a bone cavity. Rather than using a rigid needle that proceeds linearly through bone, the device includes a thin hollow needle that is flexible enough to move through the bone marrow cavity in a non-linear fashion. By advancing the needle in a non-linear path, the needle can access different locations in the bone from a single entry point.

Although the flexible needle in the '181 Patent can, in theory, allow more marrow to be collected from a single entry point, collection is only done by aspiration. The flexible needle does not allow bone marrow or tissue to be collected by "coring", in which a core of marrow is removed from the bone cavity in an undisturbed state. Aspiration tends to mix stem cells with blood and other components as the material is collected under suction. This mixing can dilute the concentration of stem cells at a collection point.

Flexible needles are also prone to breakage during procedures due to their very small diameter. This propensity for breakage often requires the use of accessories to reinforce the needle during a harvesting procedure. For example, the '181 Patent describes embodiments that utilize a stylet inside the flexible needle when the needle is advanced into the bone marrow. Stylets provide aspiration needles with additional strength and rigidity during advancement through the marrow space. The need for stylets and other accessories increases the number of items that must be sterilized and handled with aspiration needles during a harvesting procedure.

Moreover, flexible hollow needles offer few options for controlling the amount of bending or pivot motion along the length of the needle. Flexible needles with uniform cross sections are generally flexible along their entire length. This may not be desirable in applications where only a section of the shaft needs to bend, while the remainder of the shaft should remain rigid. Flexible needles also lack features to assist in cutting through dense cortical bone or shaving bone.

U.S. Pat. No. 8,852,119 to Kortney Wawrziniak, et al. (hereinafter, "the '119 Patent") describes another device for harvesting bone marrow from a bone cavity. The device includes a flexible needle and a trocar with a cannulated shaft. The cannulated shaft of the trocar can be driven into bone to provide an access path into the bone. The cannulated shaft is also configured to receive the flexible needle after being driven into the bone. Once the needle is advanced into a target bone, a receptacle is coupled to the needle to aspirate bone marrow through the needle. The needle can have both a rigid section and a flexible portion extending distally from the rigid section. The flexible portion of the needle is defined by a continuous groove that extends along a helical path.

The needle described in the '119 Patent provides some benefits over other needles that are flexible along their entire length. Nevertheless, the needle of the '119 Patent only collects bone marrow by aspiration, and does not allow bone marrow or tissue to be collected by coring. In fact, the passage inside the needle terminates short of the distal end, where the passage aligns with intake ports on the side of the needle. Moreover, the intake ports on the side of the needle are recessed to prevent material other than aspirate from entering the needle. In this arrangement, the needle passage cannot receive a core of material because the passage is essentially closed off. Therefore, the needle is limited in how it can harvest marrow and collect material inside bone.

The applicant has previously developed a collection device, assembly and procedure for more efficiently collecting tissue from bodily cavities. The collection device is a versatile instrument that can remove bone marrow material by both coring and by aspiration. The instrument functions in some instances as an auger-type tool that removes solid material in a preserved state from the body, and in other instances acts as a needle-type tool to remove liquid or fluid material by aspiration. Examples of the collection device are described in U.S. Publication No. 2018/0049727A1, the content of which is incorporated by reference herein in its entirety.

Despite developments in the area of tissue collection, there remains a need for improved collection devices that collect tissue efficiently, particularly from bone.

SUMMARY

The shortcomings of conventional devices and techniques for collecting tissue and harvesting bone marrow are resolved by a cutting tip, and a shaft incorporating the cutting tip, in accordance with the present disclosure.

In one beneficial aspect of the disclosure, an instrument for collecting tissue from a body cavity includes a hollow tubular body that defines a longitudinal axis. The tubular body can include a proximal end portion that terminates at a proximal-most end, a distal end portion that terminates at a distal-most end, and a middle section extending between the proximal end portion and the distal end portion. The middle section can have a first end contiguous with and next to the proximal end portion, and a second end contiguous with and next to the distal end portion. The tubular body can include a tubular wall extending between the proximal-most end and the distal-most end. The tubular wall can define an outer wall surface and an inner wall surface. The tubular wall can surround a passage that extends to the distal end portion of the tubular body. The distal end portion can include a core drill with a cutting tip. The cutting tip can define a first aperture, a second aperture opposite the first aperture, and a web extending between the first aperture and the second aperture. The web can taper to a drill point at the distal-most end of the tubular body.

In another beneficial aspect of the disclosure, the first aperture and the second aperture can each comprise an outline bounded by a first linear edge, a second linear edge, and third linear edge and a fourth curved edge.

In another beneficial aspect of the disclosure, the first linear edge and the second linear edge can lie in a first plane transverse to the longitudinal axis.

In another beneficial aspect of the disclosure, the third linear edge and the fourth curved edge can lie in a second plane transverse to the longitudinal axis and to the first plane.

In another beneficial aspect of the disclosure, the first plane and the second plane can intersect at a vertex line.

In another beneficial aspect of the disclosure, the first linear edge, second linear edge and vertex line can form a triangle.

In another beneficial aspect of the disclosure, the third linear edge, fourth curved edge and vertex line can form a pie-shape enclosed by two straight sides and one curved side In another beneficial aspect of the disclosure, the first aperture can be defined by a first gash having a first gash angle and the second aperture can be defined by a second gash having a second gash angle.

In another beneficial aspect of the disclosure, the first gash angle and second gash angle can each be 30 degrees relative to the longitudinal axis.

In another beneficial aspect of the disclosure, the first gash can be defined by a first gash sweep, and the second gash can be defined by a second gash sweep.

In another beneficial aspect of the disclosure, the first gash sweep and the second gash sweep can each be 125 degrees relative to the longitudinal axis.

In another beneficial aspect of the disclosure, the first aperture can be defined by a first lip having a first lip relief, and the second aperture can be defined by a second lip having a second lip relief.

In another beneficial aspect of the disclosure, the first lip relief and second lip relief can each be 15 degrees.

In another beneficial aspect of the disclosure, the web can include an inner web surface, an outer web surface, and a web thickness between the inner web surface and the outer web surface.

In another beneficial aspect of the disclosure, the web thickness at the drill point can be 0.035 in.

In another beneficial aspect of the disclosure, the cutting tip can define an outer drill point angle and an inner core angle.

In another beneficial aspect of the disclosure, the outer drill point angle and the inner core angle can be equal.

In another beneficial aspect of the disclosure, the outer drill point angle and the inner core angle can be 118 degrees.

In another beneficial aspect of the disclosure, the drill point can include a linear edge.

In another beneficial aspect of the disclosure, the linear edge can have a length of 0.015 in.

In another beneficial aspect of the disclosure, the passage can terminate at the proximal end to define a proximal opening in the tubular body, and can terminate at the distal end to define the first and second apertures.

In another beneficial aspect of the disclosure, the tubular body can include an articulating section that allows a portion of the tubular body to articulate relative to the proximal end portion.

In another beneficial aspect of the disclosure, the articulating section can include a plurality of interlocking sections.

In another beneficial aspect of the disclosure, the articulating section can include a first interlocking section and a second interlocking section.

In another beneficial aspect of the disclosure, the first interlocking section and second interlocking section can each have at least one pin and at least one socket.

In another beneficial aspect of the disclosure, the at least one pin can be substantially triangular shaped, and the at least one socket can be substantially triangular shaped.

In another beneficial aspect of the disclosure, the at least one pin on the first interlocking section can have a circumferential width that increases as said at least one pin on the first interlocking section extends from the outer surface of the shaft to the inner surface of the shaft, so that said at least one pin on the first interlocking section becomes gradually wider toward the inner surface.

In another beneficial aspect of the disclosure, the at least one pin on the second interlocking section can have a circumferential width that decreases as said at least one pin on the second interlocking section extends from the outer surface of the shaft to the inner surface of the shaft, so that said at least one pin on the second interlocking section becomes gradually narrower toward the inner surface.

In another beneficial aspect of the disclosure, the first and second interlocking sections can be cut at opposing angles to create at least one inward angled surface and at least one outward angled surface, said at least one inward angled surface being adjacent to the at least one outward angled surface.

In another beneficial aspect of the disclosure, the tubular body can have a uniform outer diameter along an entire length of the tubular body such that outer diameters of the proximal end portion, middle section and distal end portion are equal.

In another beneficial aspect of the disclosure, the tubular body can be a one-piece body of unitary construction.

In another beneficial aspect of the disclosure, the one-piece body of unitary construction can be bendable.

In another beneficial aspect of the disclosure, the one-piece body of unitary construction can be non-bendable.

In another beneficial aspect of the disclosure, the passage can extend from the proximal end portion of the tubular body to the distal end portion of the tubular body.

In another beneficial aspect of the disclosure, the web can include a first web section and a second web section.

In another beneficial aspect of the disclosure, the first and second web section can each have a pie-wedge shape.

BRIEF DESCRIPTION OF THE DRAWINGS

The summary and detailed description sections will be better appreciated when reviewed in conjunction with the drawing figures. The following drawing figures illustrate exemplary and non-limiting embodiments of the present disclosure, and depict elements which can be combined and arranged either as shown, or in other combinations and arrangements that are contemplated by persons of skill in the art.

DETAILED DESCRIPTION

Figure 1:
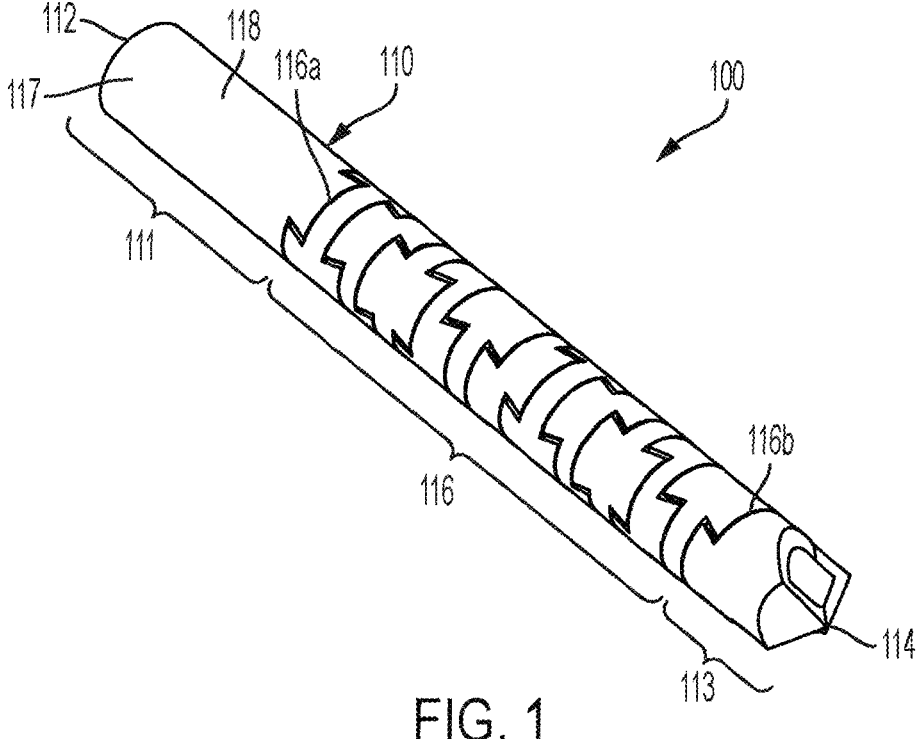
FIG. 1 is a perspective view of a tissue collection instrument according to one example.

The term "proximal-most end" as used herein refers to a point on an object that is located most proximal compared to all other points on the object, or in the case of multiple points being positioned most proximal when compared to all other points on the object, the term refers to the edge or surface made up of those multiple points.

The term "distal-most end" as used herein refers to a point on an object that is located most distal compared to all other points on the object, or in the case of multiple points being positioned most distal when compared to all other points on the object, the term refers to the edge or surface made up of those multiple points.

For purposes of this description, the collection device and cutting tip will be described as they would be used for collecting bone marrow from bone. When used for collecting bone marrow, the bone marrow can be collected for biopsy purposes, for use as a medium for bony regeneration, or for harvesting stem cells to be processed and used for the subsequent treatment of congenital defects, diseases or other conditions.

The collection device features a cannulated shaft that allows for safe and efficient collection of bone marrow from a single entry point into the bone. The shaft can be a rigid (i.e. non-bending) shaft, such as a stiff shaft having a one-piece unitary construction. Alternatively, the shaft can be a flexible shaft with at least one section that can bend. The flexible shaft can be comprised of rigid components, including rigid interlocking segments that collectively form a flexible section. The rigid segments allow the shaft to be advanced though bone marrow without the need for a stylet or other type of structural reinforcement in or around the shaft. The flexible section allows the shaft to yield and bend as it advances through marrow, so as to follow a path of least resistance. Thus, after penetrating through the outer cortex, the flexible shaft can bend and advance along the inner aspect of the bone where higher concentrations of stem cells are found.

Providing flexibility in the shaft can also prevent the leading end of the shaft from penetrating through a bone wall opposite an entry point, because the flexible section causes the leading end to bend in response to contact with the bone wall. This provides a safe alternative to rigid needles, particularly when used in long bones or other areas in which the cavities are relatively narrow or confined.

The shaft, whether flexible or non-bending, can include a distal shaving tip with bone shaving features not present on conventional needles. The shaving features aid in cutting and displacing bone from the outer cortex during initial penetration into the bone. The shaving features can also allow the shaft to cleanly remove a core of bone marrow material when advanced into an area containing a high concentration of stem cells. The core of material is cut cleanly from the surrounding material as the distal shaving tip moves through the material, yielding a core with a high concentration of stem cells preserved inside. By allowing a core of bone marrow to be removed, the stem cells are not diluted or mixed with blood and other matter. This avoids the need to employ subsequent processing such as centrifugation in order to separate the stem cells from other material.

Figure 2:
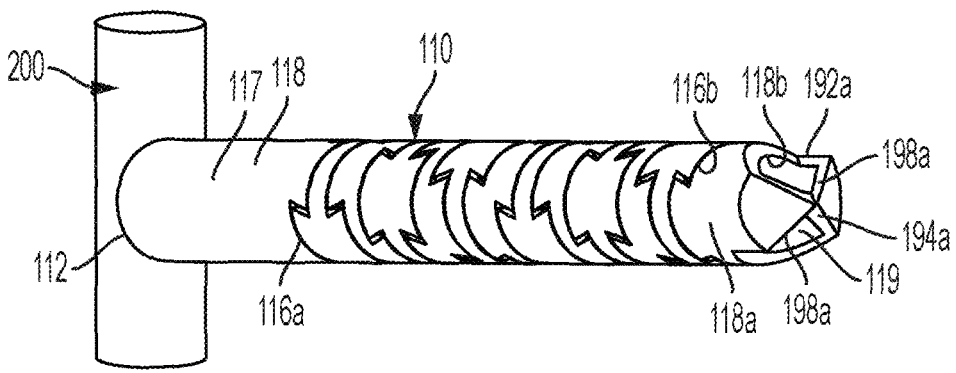
FIG. 2 is a perspective view of a tissue collection instrument according to another example with a handle attached to the instrument.

Referring now to FIG. 1, a collection instrument 100 for collecting tissue from a body cavity will be described in accordance with one embodiment. Collection instrument 100 features a hollow tubular body in the form of a hollow shaft 110. Shaft 110 can be formed of any suitable medical grade material approved for surgical instrumentation, including but not limited to stainless steel. Shaft 110 includes a proximal end portion 111 that terminates at a proximal-most end 112. Proximal-most end 112 can be attached to a handle or other structure for operating collection instrument 100, which can be operated manually and/or with a power tool attached. FIG. 2 shows a similar shaft 110 attached to a T-bar 200. Various other handle configurations can also be used.

Shaft 110 includes a distal end portion 113 that terminates at a distal-most end 114. Shaft 110 also includes a middle section 116 extending between proximal end portion 111 and distal end portion 113. Middle section 116 includes a first end 116*a* contiguous with and next to proximal end portion 111, and a second end 116*b* contiguous with and next to distal end portion 113. Shaft 110 also features a tubular wall 118 extending between proximal-most end 112 and distal-most end 114. Tubular wall 118 defines an outer wall surface 118*a* and an inner wall surface 118*b*. In addition, tubular wall 118 defines and surrounds a passage 119 that is circular in cross section. Passage 119 extends from proximal-most end 112 of shaft 110 to distal-most end 114 of the shaft.

The lengths of shaft 110, proximal end portion 111, middle section 116 and distal end portion 113 are not shown to scale. Therefore, it will be understood that the relative length of each section, and the length of the shaft as a whole, are not necessarily represented by the relative dimensions shown in the drawings. For example, proximal end portion 111 can be much longer relative to middle section 116 and distal end portion 113 than the relative length that appears in the Figures.

Figure 3:
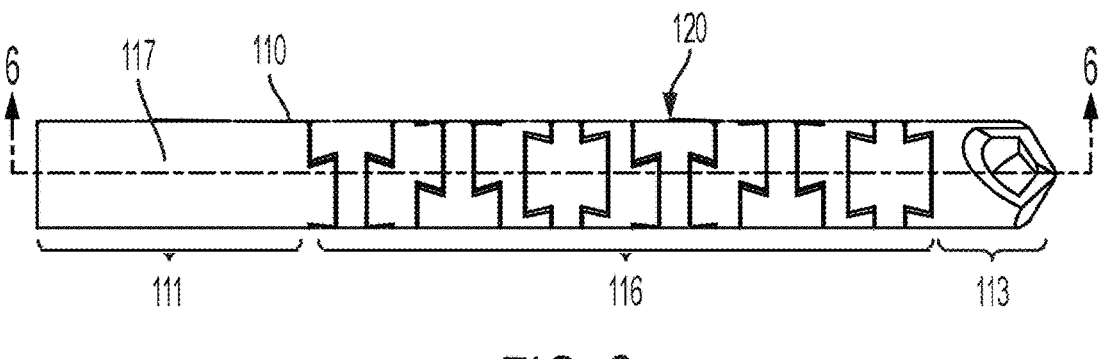
FIG. 3 is a side view of the tissue collection instrument of FIG. 1.
Figure 4:
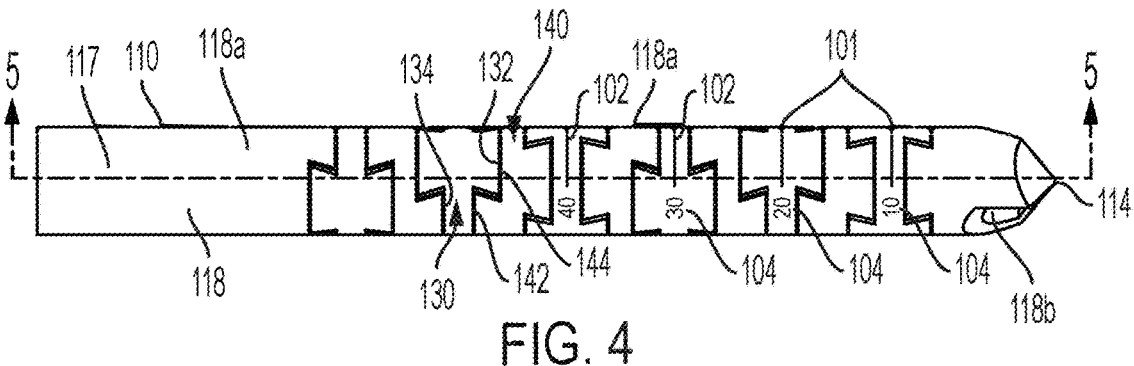
FIG. 4 is another side view of the tissue collection instrument of FIG. 1.

Referring to FIGS. 3 and 4, middle section 116 of shaft 110 includes an articulating section 120 that allows distal end portion 113 and a portion of the middle section to articulate or bend relative to proximal end portion 111. Articulating sections in accordance with the present disclosure can feature a variety of constructs that allow shaft 110 to articulate or bend. In one preferred embodiment, the articulating section includes a plurality of interlocking segments or elements, such as interlocking sections of the type and arrangement described in U.S. Pat. No. 8,366,559 entitled "Cannulated Flexible Drive Shaft", the content of which is incorporated by reference herein in its entirety and for all purposes. For example, the articulating section can incorporate a FlexMetric® brand flexible surgical shaft marketed by Lenkbar, LLC of Naples, Florida, USA.

Articulating section 120 includes a first interlocking section 130 and a second interlocking section 140. First interlocking section 130 has at least one pin 132 and at least one socket 134. Likewise, second interlocking section 140 has at least one pin 142 and at least one socket 144. Each pin is substantially triangular or trapezoidal shaped, and each socket is substantially triangular or trapezoidal shaped, having the same general shape as the corresponding pin. Pin 132 on first interlocking section 130 has a circumferential width that increases uniformly (i.e. at a constant rate) from outer wall surface 118a to inner wall surface 118b, so that the pin becomes gradually wider as it extends radially inwardly toward a longitudinal axis L of shaft 110, which is identified in FIG. 5. Pin 142 on second interlocking section 140 has a circumferential width that decreases uniformly (i.e. at a constant rate) from outer wall surface 118a to inner wall surface 118b, so that the pin becomes gradually narrower as it extends radially inwardly toward longitudinal axis L of shaft 110. The first and second interlocking sections 130 and 140 are cut at opposing angles to create at least one inward angled surface and at least one outward angled surface, the inward angled surface being adjacent to the outward angled surface.

Figure 5:
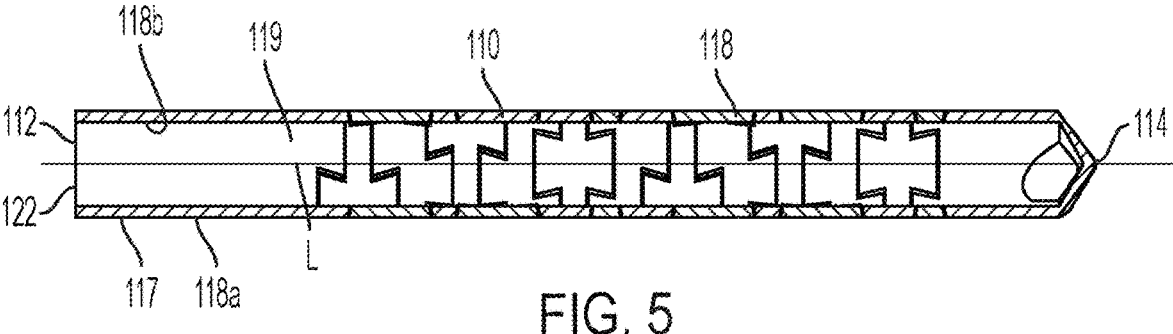
FIG. 5 is a side cross sectional view of the tissue collection instrument of FIG. 1 taken through line 5-5 in FIG. 4.
Figure 6:
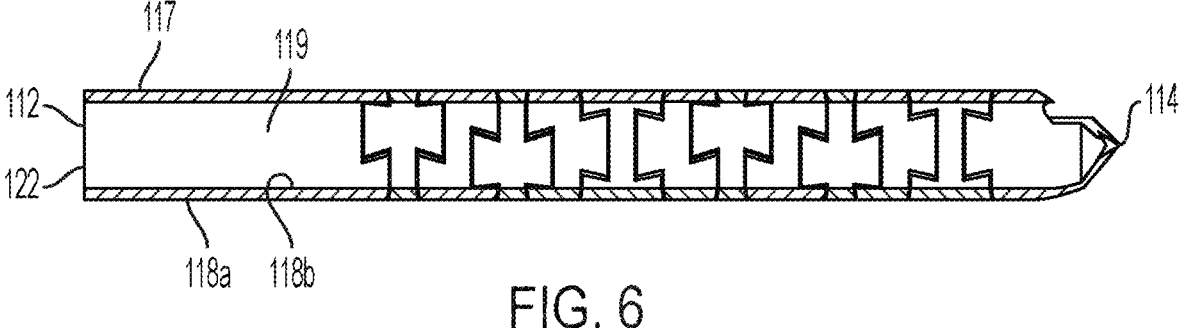
FIG. 6 is a side cross sectional view of the tissue collection instrument of FIG. 1 taken through line 6-6 in FIG. 3.

Shafts according to the present disclosure can be cannulated, with passages defined in various configurations. Referring to FIGS. 5 and 6, passage 119 terminates at proximal-most end 112 to define a proximal opening 122 in shaft 110. It should be noted that proximal-most end 112 is shown as a smooth cylinder end, but could have various internal and/or external geometries for coupling to handles, power tools and other accessories. For example, proximal-most end 112 could have one or more flat portions on the exterior configured to fit into a hexagonal or polygon-shaped socket formed in a handle shaft.

Figure 7:
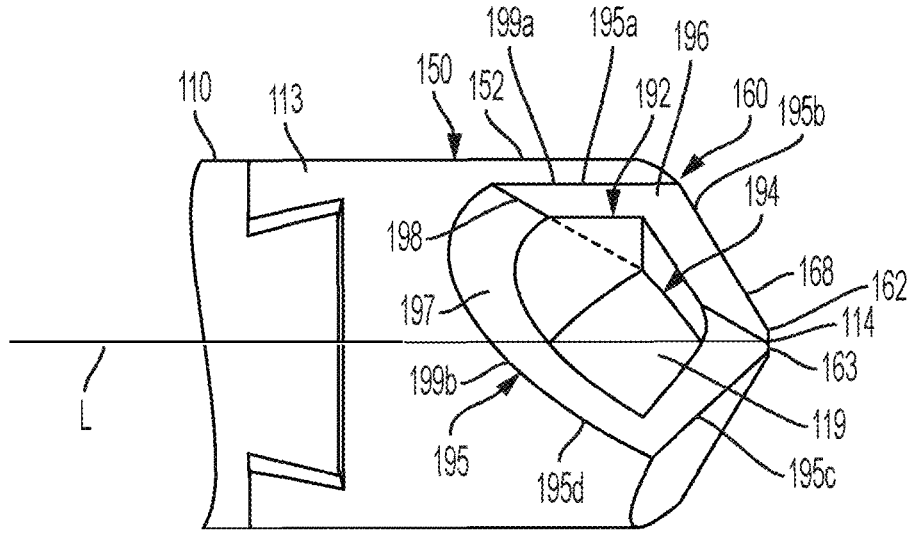
FIG. 7 is an enlarged truncated view of a distal end portion of the tissue collection instrument of FIG. 1.
Figure 8:
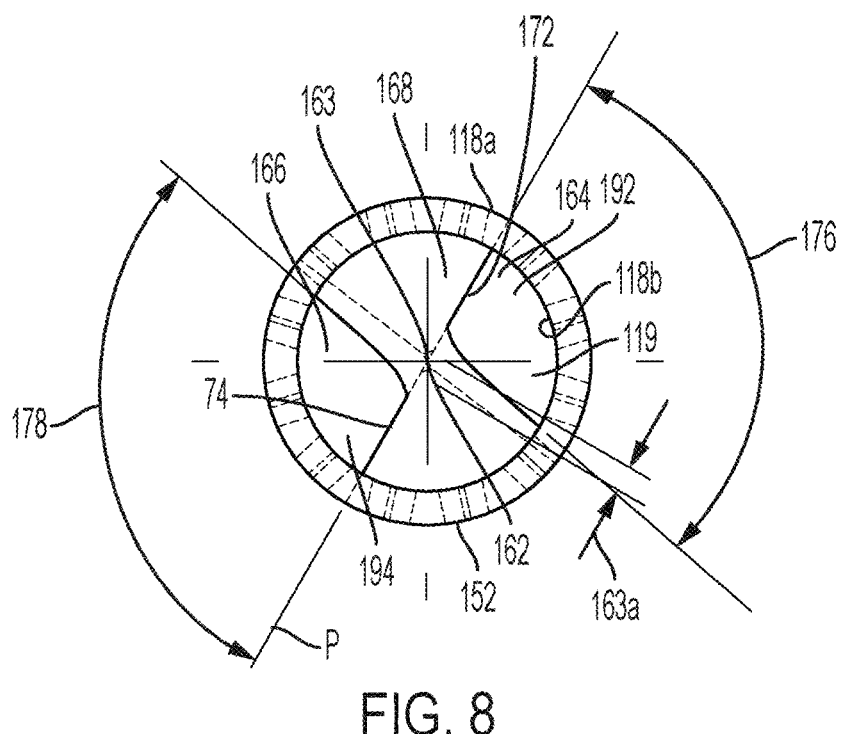
FIG. 8 is an end view of the tissue collection instrument of FIG. 1.

Referring to FIGS. 7 and 8, passage 119 terminates at distal-most end 114, forming a first aperture 192 and a second aperture 194. First and second apertures 192, 194 are configured to receive bone marrow and other materials through distal-most end 114 as shaft 110 is advanced into bone. Inner wall surface 118b forms a smooth, continuous and uninterrupted annular surface around passage 119 and adjacent to the first and second apertures 192, 194. This smooth surface slidingly receives material that enters first and second apertures 192, 194, while minimizing frictional forces and shear stresses, so that the material is removed cleanly and in a preserved state.

Distal end portion 113 and first and second apertures 192, 194 form a core drill 150 that shaves bone and cuts smoothly through bone marrow. Core drill 150 has a cylindrical outer wall 152 which coincides with and is coextensive with outer wall surface 118a of shaft. Thus, the outer diameter of core drill 150 is equal to the outer diameter of shaft 110. Shaft 110 can be used to remove bone marrow material by a coring technique. In addition, shaft 110 can be used to remove bone marrow by aspiration. As such, shaft 110 functions in some instances as an auger-type tool that removes solid material in a preserved state from the body, and in other instances acts as a needle-type tool to remove liquid or fluid material by aspiration. Where aspiration is performed, the first and second apertures 192, 194 can function as suction ports to remove fluid material from a bone cavity under negative pressure.

Core drill 150 features a cutting tip 160. Cutting tip 160 is a distal shaving tip with bone shaving features that aid in cutting and displacing bone from the outer cortex during initial penetration into the bone. The shaving features also allow the shaft to cleanly remove a core of bone marrow material when advanced into an area containing a high concentration of stem cells. The core of material is cut cleanly from the surrounding material as the distal shaving tip moves through the material, yielding a core with a high concentration of stem cells preserved inside shaft 110.

Cutting tip 160 defines a drill point 162 at distal-most end 114 of shaft 110. Drill point 162 has a linear edge 163 that extends perpendicularly to longitudinal axis L. Edge 163 has an edge length 163a. A first gash 164 is formed in cutting tip 160, and a second gash 166 is formed on the opposite side of the cutting tip. First gash 164 is defined by a first gash sweep 176, and second gash 166 is defined by a second gash sweep 178 equal to first gash sweep 176. A web 168 extends between first and second gashes 164, 166, forming a section of solid material between first and second apertures 192, 194. Web 168 extends radially outwardly and terminates at outer wall 152 of core drill 150.

Figure 9:
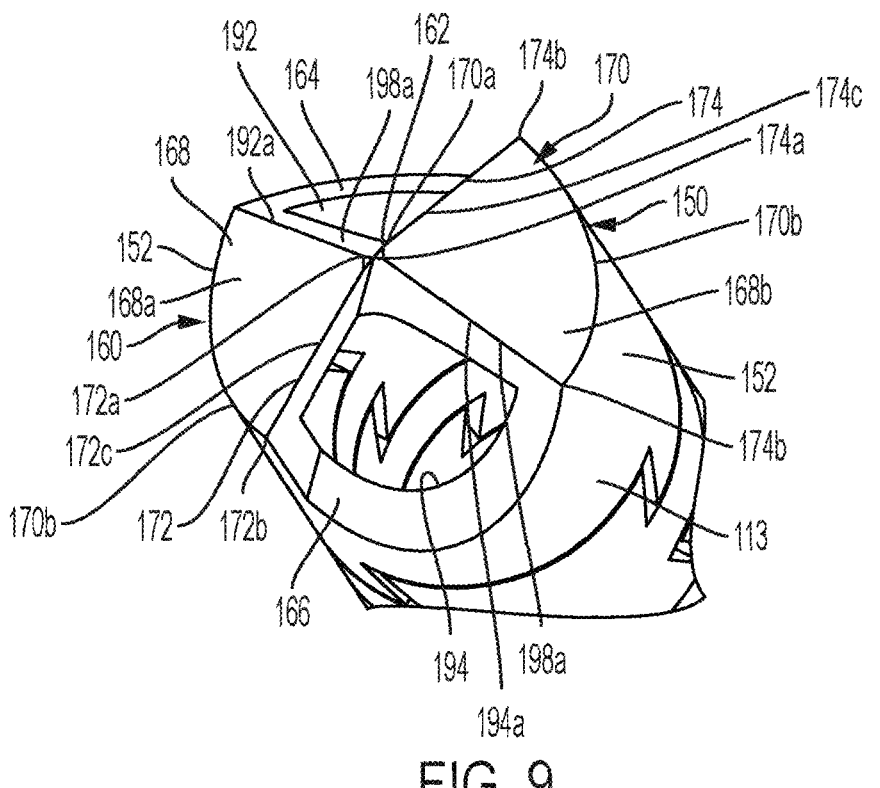
FIG. 9 is an enlarged truncated perspective view of the tissue collection instrument of FIG. 1.

Referring to FIG. 9, first gash 164 defines a first lip 172. First lip 172 has an inner lip end 172a terminating at point 162 and an outer lip end 172b terminating at outer wall 152. Similarly, second gash 166 defines a second lip 174. Second lip 174 has an inner lip end 174a terminating at drill point 162 and an outer lip end 174b terminating at outer wall 152. First lip 172 and second lip 174 form first and second cutting edges 172c, 174c respectively that extend outwardly from drill point 162 to outer wall 152.

Web 168 has an end profile 170 with a narrow section 170a in the center and two wider ends 170b, forming a bow-tie or hourglass shape. The bow-tie shape includes a first web section 168a and a second web section 168b. First and second web sections 168a, 168b converge toward one another as they extend toward drill point 162. In addition, first and second web sections 168a, 168b each define a pie wedge shape. First lip 172 and second lip 174 are coplanar and conform to a plane P that passes through drill point 162, as shown in FIG. 8.

Figure 10:
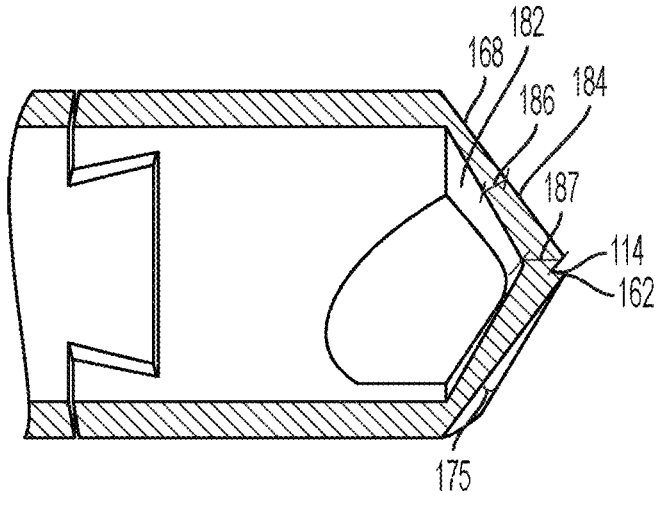
FIG. 10 is an enlarged truncated cross section view of the distal end portion of the tissue collection instrument of FIG. 1.
Figure 11:
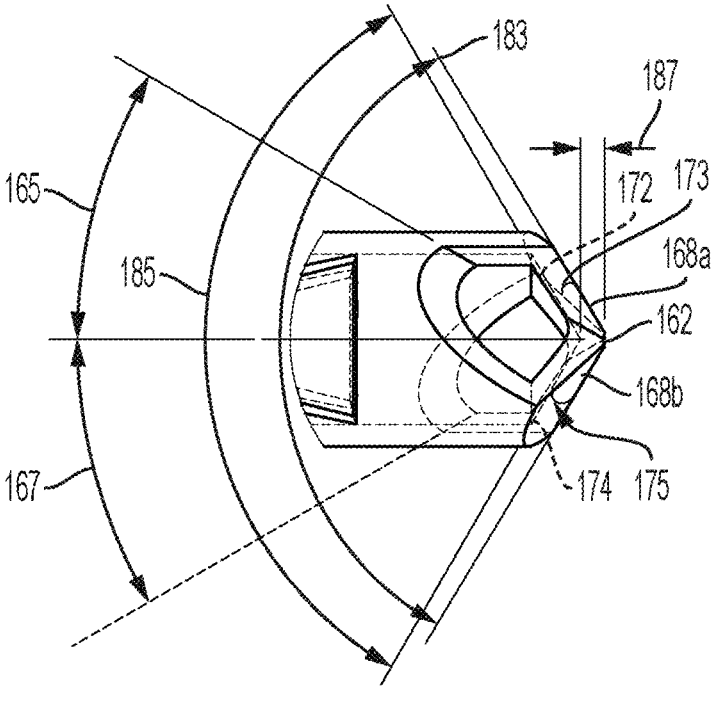
FIG. 11 is another enlarged truncated view of a distal end portion of the tissue collection instrument of FIG. 1, with broken lines showing certain features on the side not visible.

Referring to FIGS. 10 and 11, web 168 has an inner web surface 182 and an outer web surface 184. The shaft material between inner web surface 182 and outer web surface 184 defines a web thickness 186. Web thickness 186 at drill point 162 defines a point thickness 187. Point thickness 187 is greater than edge length 163a, the latter being shown in FIG. 8. Distal-most end 114 defines a drill point angle 183 which is the outer tip angle including drill point 162. Drill point angle 183 is the angle of taper between first web section 168a and second web section 168b. Distal-most end 114 also defines a core angle 185 that is the total or included angle between first lip 172 and second lip 174. The drill point angle 183 and core angle 185 can be the same or slightly different.

First lip 172 has a first lip relief angle 173, and second lip 174 has a second lip relief angle 175. First lip relief angle 173 is equal to second lip relief angle 175. First gash 164 defines a first gash angle 165 and second gash 166 defines a second gash angle 167. First gash angle 165 is the angle ground to create first aperture 192, and second gash angle 167 is the angle ground to create the second aperture 194.

Cutting tips according to the present disclosure can have various dimensions, lip relief angles, gash sweep angles, and other geometric specifications. Table 1 lists one set of specifications that can be implemented in a cutting tip example according to the present disclosure.

TABLE 1

| Cutting Tip Example | |
| --- | --- |
| First lip relief angle | 15° |
| Second lip relief angle | 15° |
| Drill point angle | 118° |
| Core angle | 118° |
| First gash sweep angle | 125° |
| Second gash sweep angle | 125° |
| First gash angle | 30° linear |
| Second gash angle | 30° linear |
| Edge length | 0.015 in. |
| Point thickness | 0.035 in. |

Referring back to FIG. 7, first and second apertures 192, 194 each have an outline 195 bounded by four edges. In particular, each outline 195 includes a first linear edge 195a, a second linear edge 195b, a third linear edge 195c and a fourth curved edge 195d. First linear edge 195a and second linear edge 195b lie in a first plane 196. Third linear edge 195c and fourth curved edge 195d lie in a second plane 197 that intersects first plane 196 at a vertex line 198. A portion of vertex line 198 that crosses aperture 192 is shown in broken line. First plane 196 extends transversely to longitudinal axis L. Second plane 197 extends transversely to longitudinal axis L and to first plane 196. In particular, first plane 196 intersects second plane 197 at an obtuse angle, forming a V-shaped end profile 198a. Thus, aperture 192 and its respective edges form a V-shaped notch 192a, and aperture 194 and its respective edges form a V-shaped notch 194a as shown in FIGS. 2 and 9. V-shaped notches 192a, 194a intersect at their vertices.

First linear edge 195a, second linear edge 195b and vertex line 198 define a triangle 199a. Third linear edge 195c, fourth curved edge 195d and vertex line 198 define a pie-shape 199b enclosed by two straight sides and one curved side. Triangle 199a and pie-shape 199b intersect along vertex line 198, a portion of which that crosses aperture is shown in broken line. This geometry of first and second apertures 192, 194 has been found to efficiently collect bone marrow.

Tissue collection instruments in accordance with the present disclosure can have a variety of handle configurations to be gripped by a physician, as described previously. Handle portions in accordance with the present disclosure can be connected to shafts using any suitable connection, such as a pinned connection, a molded connection, or other alternative. In preferred embodiments, a handle portion is provided at the proximal end of the tissue collection instrument. The preferred handle portion is ergonomically configured to permit the physician to comfortably grip the instrument and manually apply different types of force to the shaft via the handle. These forces can include pushing and pulling forces to advance and withdraw the shaft, respectively, as well as twisting forces to rotate the shaft. Certain combinations of pushing force and twisting force can also induce bending of shaft 110 at the articulation section 120 during advancement of the shaft through the bone cavity.

Collection devices in accordance with the present disclosure can also include one or more features that assist the physician with visually monitoring the depth of insertion of the shaft inside the body. In FIG. 4, for example, shaft 110 includes a plurality of indicia 101 that are provided along outer wall surface 118a. Indicia 101 can be produced by any suitable process, including but not limited to laser cutting, laser marking, etching, or other means. Various types of indicia can be provided in accordance with the present disclosure. For example, indicia 101 include a first indicia in the form of incrementally spaced hash marks or lines 102. Lines 102 extend circumferentially around outer wall surface 118a. Indicia 101 also include a second indicia in the form of numberings 104. Each numbering 104 is located adjacent to one of the lines 102 and corresponds to that line. The value of each numbering 104 represents a depth of insertion in centimeters. Each numbering 104 is an integer that represents the distance between its respective line 102 and distal-most end 114 of shaft 110. When shaft 110 is advanced into an incision, and a line 102 aligns with the patient's skin surface, the numbering 104 corresponding to that line at the skin surface indicates the depth to which distal-most end 114 is advanced into the body.

Shafts in accordance with the present disclosure can feature articulating sections that span a small fraction of the shaft's overall length, or a large fraction of the shaft's overall length, so as to provide a desired degree of bending, i.e. a desired "pivot cone". For example, the longitudinal length of articulating section 120 can be one-quarter or 25% of the total length of shaft 110. Therefore, 25% of the shaft length is comprised of interlocking segments that allow distal-most end 114 to bend and pivot with respect to proximal-most end 112. The remaining three-quarters or 75% of the total length of shaft 110 is a solid unitary section 117 that remains fixed in its orientation. Therefore, proximal end portion 111 and a majority of middle portion 116 can be fixed in orientation, providing structural reinforcement that allows the shaft to be advanced through bone and tissue and maintain trajectory without buckling.

The length of the flexible section versus the length of the solid unitary section can of course be different in other embodiments. For example, a larger percentage of the length can be devoted to the articulating section to allow for a greater degree of bending and pivot motion. Alternatively, a smaller percentage of the length can be devoted to the articulating section to allow for a smaller degree of bending and pivot motion. As such, the length of the articulating section can be any percentage of the total length of the shaft, including but not limited to 5%, 10%, 15%, 20%, 25%, 30%, 35%, 40%, 45%, 50%, 55%, 60%, 65%, 70%, 75%, or 80% of the total length of the shaft. Percentages less than 5% or greater than 80% can also be used. Choosing a specific percentage allows the shaft's flexibility and pivot cone to be precisely controlled, unlike conventional flexible needles that are flexible along their entire lengths.

Example—Bone Marrow Harvesting Procedure

Figure 12:
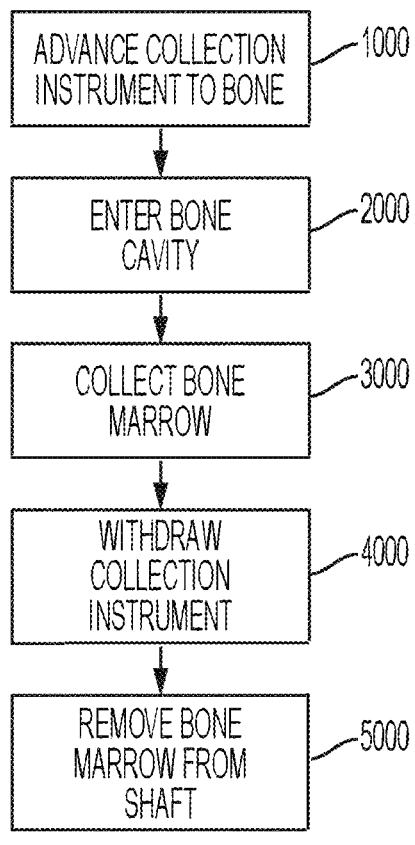
FIG. 12 is a block diagram showing steps of a tissue collection procedure according to one example.

Referring to FIG. 12, one possible tissue collection procedure in accordance with the present disclosure is shown in block diagram form. In this example, the procedure is a bone marrow harvesting procedure in which bone marrow and stems cells are collected from a patient's anterior or posterior ilium. The previously described collection instruments will be referenced when describing individual steps. Other devices can also be used to carry out the method in accordance with the present disclosure. In addition, the steps can be performed with or without additional steps known to physicians and medical professionals of ordinary skill in the art.

In step 1000, tissue collection instrument 100 is inserted into an incision and advanced to an exposed bone surface of the ilium. Prior to this step, the physician may apply an anti-coagulant to surfaces on tissue collection instrument 100 to prevent matter from clotting, particularly on the inside of the collection instrument. The physician may also prepare a small hole in the bone surface using a piercing instrument. Once tissue collecting instrument 100 is inserted, drill point 162 of cutting tip 160 is placed on the desired entry point through the bone. The physician then presses their hand or palm firmly against proximal-most end 112, which may have a handle, knob, palm rest or other structure to receive force from the physician's hand or palm. The physician then applies axial pressure to proximal-most end 112 while rotating the proximal end in a clockwise direction. Tissue collection instrument 100 is rotated while axial pressure is maintained to manually drive cutting tip 160 and shaft 110 through the cortical bone. The simultaneous application of axial pressure and rotation are continued until cutting tip 160 completely penetrates through the cortical bone and enters the cavity in step 2000. The moment of entry into the cavity can be sensed through tactile feel, as the amount of resistance to axial advancement drops the moment that the cortical bone is fully penetrated and no longer provides resistance. Entry into the bone cavity can also be confirmed using imaging.

Once cutting tip 160 enters the bone cavity, the tissue collection instrument is used in a coring mode to collect a core of bone marrow in step 3000. The handle is simultaneously twisted and advanced to collect the bone marrow. Shaft 110 has a moderate amount of freedom to bend. Nevertheless, the degree of flexibility of articulating section 120 is limited, so that shaft 110 is able to advance through bone marrow, albeit not in a straight path. The limited flexibility of articulating section 120 causes distal end portion 113 to yield under resistance as it advances through marrow and/or contacts the inner aspect of the bone. This results in a bending movement that alters the direction of advancement as the collection instrument 100 is advanced, which prevents inadvertent penetration beyond the marrow space, adding a safety advantage to the process.

Tissue collection device 100 is simultaneously advanced and rotated through the bone like an auger until a core of bone marrow in the path of movement is collected inside passage 119 of shaft 110. Shaft 110 is advanced into the ilium to a desired depth corresponding to the desired amount of marrow to be removed. For example, shaft 110 can be inserted to a depth of 3-4 cm. Once shaft 110 reaches the desired depth, further advancement is halted and the tissue collection device 100 is withdrawn from the patient in step 4000. The core of bone marrow inside shaft 110 is then carefully removed from the shaft in step 5000. The bone marrow can be removed from the shaft using a suitable instrument, such as a piercing instrument or other implement that can dislodge the core of bone marrow from passage 119.

The removal of bone marrow from the bone can leave a void space in the bone cavity. Bone marrow in and around the void space can be agitated during removal of collection instrument 100 from the bone cavity. This agitation can leave a fluid dispersion of stem cells and blood cells in the void space. At this stage, collection instrument 100 can be attached to a source of negative pressure, such as a syringe, and operated in an aspiration mode to collect the stem cells dispersed in and around the void space. Collection instrument 100 is reinserted back through the same incision and entry point of the bone, and into the void space to collect the dispersed stem cells.

Although the present disclosure describes and illustrates specific embodiments, the present disclosure is not intended to be limited to the details shown. Rather, various modifications, combinations, substitutions and/or rearrangements can be made with respect to the components and their features shown herein, with any such modification, combination, substitution and/or rearrangement being contemplated within the scope and range of equivalents of the claims and without departing from the present disclosure.

For example, collection instruments according to the present disclosure need not have a flexible shaft, as noted previously, but can also feature a non-bending shaft, such as a stiff shaft having a one-piece unitary construction. An example of a stiff shaft having a one-piece unitary construction would look identical to shaft 110 shown in the drawing figures, but the cut lines defining the interlocking sections would be absent and replaced with solid wall.

Collection instruments according to the present disclosure also need not have only two apertures, but could also feature fewer or more apertures. For example, collection instruments according to the present disclosure could feature three, four, five, six or more apertures arranged circumferentially around core drill 150.

What is claimed:

1. An instrument for collecting tissue from a body cavity, the collection instrument comprising:
   a hollow tubular body that defines a longitudinal axis, the tubular body comprising a proximal end portion that terminates at a proximal-most end, a distal end portion that terminates at a distal-most end, and a middle section extending between the proximal end portion and the distal end portion, the middle section having a first end contiguous with and next to the proximal end portion, and a second end contiguous with and next to the distal end portion, the tubular body comprising a tubular wall extending between the proximal-most end and the distal-most end, the tubular wall defining an outer wall surface and an inner wall surface, the tubular wall surrounding a passage that extends to the distal end portion of the tubular body,
   wherein:
   the distal end portion comprises a core drill with a cutting tip, the cutting tip defining a first aperture, a second aperture opposite the first aperture, and a web extending between the first aperture and the second aperture, the web tapering to a drill point at the distal-most end of the tubular body, the first aperture and the second aperture each comprise an outline bounded by a linear first edge, a linear second edge, a linear third edge, and a curved fourth edge,
   the linear first edge and the linear second edge lie in a first plane extending along the longitudinal axis, and
   the linear third edge and the curved fourth edge lie in a second plane transverse to the longitudinal axis and transverse to the first plane.

2. The instrument according to claim 1, wherein the first aperture and the second aperture each comprise an outline bounded entirely by the linear first edge, the linear second edge, the linear third edge and the curved fourth edge.

3. The instrument according to claim 1, wherein the first plane is parallel to the longitudinal axis.

4. The instrument according to claim 1, wherein the first plane and the second plane intersect at a vertex line.

5. The instrument according to claim 4, wherein the linear first edge, the linear second edge, and the vertex line form a triangle.

6. The instrument according to claim 4, wherein the linear third edge, the curved fourth edge, and the vertex line form a pie-shape enclosed by two straight sides and one curved side.

7. The instrument according to claim 1, wherein the first aperture is defined by a first gash having a first gash angle and the second aperture is defined by a second gash having a second gash angle.

8. The instrument according to claim 7, wherein the first gash angle and second gash angle are each 30 degrees relative to the longitudinal axis.

9. The instrument according to claim 7, wherein the first gash is defined by a first gash sweep, and the second gash is defined by a second gash sweep.

10. The instrument according to claim 9, wherein the first gash sweep and the second gash sweep are each 125 degrees relative to the longitudinal axis.

11. The instrument according to claim 1, wherein the first aperture is defined by a first lip having a first lip relief and the second aperture is defined by a second lip having a second lip relief.

12. The instrument according to claim 11, wherein the first lip relief and second lip relief are each 15 degrees.

13. The instrument according to claim 1, wherein the web comprises an inner web surface, an outer web surface, and a web thickness between the inner web surface and the outer web surface, the web thickness at the drill point being 0.035 in.

14. The instrument according to claim 1, wherein the cutting tip defines an outer drill point angle and an inner core angle.

15. The instrument according to claim 14, wherein the outer drill point angle and the inner core angle are equal.

16. The instrument according to claim 15, wherein the outer drill point angle and the inner core angle are 118 degrees.

17. The instrument according to claim 1, wherein the drill point comprises a linear edge.

18. The instrument according to claim 17, wherein the linear edge has a length of 0.015 in.

19. The instrument according to claim 1, wherein the passage terminates at the proximal end to define a proximal opening in the tubular body, and terminates at the distal end to define the first and second apertures.

20. The instrument according to claim 1, wherein the tubular body comprises an articulating section that allows a portion of the tubular body to articulate relative to the proximal end portion.

21. The instrument according to claim 20, wherein the articulating section comprises a plurality of interlocking sections.

22. The instrument according to claim 20, wherein the articulating section comprises a first interlocking section and a second interlocking section.

23. The instrument according to claim 22, wherein each of the first interlocking section and second interlocking section has at least one pin and at least one socket.

24. The instrument according to claim 23, wherein the at least one pin is substantially triangular shaped, and the at least one socket is substantially triangular shaped.

25. The instrument according to claim 24, wherein the at least one pin on the first interlocking section has a circumferential width that increases as said at least one pin on the first interlocking section extends from the outer surface of the tubular body to the inner surface of the tubular body, so that said at least one pin on the first interlocking section becomes gradually wider toward the inner surface.

26. The instrument according to claim 24, wherein the at least one pin on the second interlocking section has a circumferential width that decreases as said at least one pin on the second interlocking section extends from the outer surface of the tubular body to the inner surface of the tubular body, so that said at least one pin on the second interlocking section becomes gradually narrower toward the inner surface.

27. The instrument according to claim 22, wherein the first and second interlocking sections are cut at opposing angles to create at least one inward angled surface and at least one outward angled surface, said at least one inward angled surface being adjacent to the at least one outward angled surface.

28. The instrument according to claim 22, wherein the tubular body has a uniform outer diameter along an entire length of the tubular body such that outer diameters of the proximal end portion, middle section and distal end portion are equal.

29. The instrument according to claim 1, wherein the tubular body comprises a one-piece body of unitary construction.

30. The instrument according to claim 29, wherein the one-piece body of unitary construction is bendable.

31. The instrument according to claim 29, wherein the one-piece body of unitary construction is non-bendable.

32. The instrument according to claim 1, wherein the passage extends from the proximal end portion of the tubular body to the distal end portion of the tubular body.

33. The instrument according to claim 1, wherein the web comprises a first web section and a second web section, the first and second web section each having a pie-wedge shape.

* * * * *